(12) United States Patent
Dener

(10) Patent No.: US 8,431,733 B2
(45) Date of Patent: Apr. 30, 2013

(54) PROCESS FOR THE PREPARATION OF (3S)-3-AMINO-N-CYCLOPROPYL-2-HYDROXYALKANAMIDE DERIVATIVES

(75) Inventor: Jeffrey Dener, Millbrae, CA (US)

(73) Assignee: Virobay, Inc., Menlo Park, CA (US)

( * ) Notice: Subject to any disclaimer, the term of this patent is extended or adjusted under 35 U.S.C. 154(b) by 662 days.

(21) Appl. No.: 12/402,312

(22) Filed: Mar. 11, 2009

(65) Prior Publication Data

US 2009/0234127 A1     Sep. 17, 2009

Related U.S. Application Data

(60) Provisional application No. 61/035,992, filed on Mar. 12, 2008.

(51) Int. Cl.
*C07C 229/00* (2006.01)
*C07C 237/02* (2006.01)

(52) U.S. Cl.
USPC ............ 562/443; 562/444; 562/450; 564/193

(58) Field of Classification Search .................. 564/193; 562/443, 444, 450
See application file for complete search history.

(56) References Cited

U.S. PATENT DOCUMENTS 2,991,307 A * 7/1961 Amiard et al. ................. 562/401
6,010,733 A * 1/2000 Takemoto et al. ............ 426/548
6,365,754 B1   4/2002 Furukawa et al.
7,138,547 B2 * 11/2006 Acena et al. .................. 564/219
2007/0054864 A1   3/2007 Graupe et al.

FOREIGN PATENT DOCUMENTS

| EP | 1 464 638 A1 | 10/2004 |
| EP | 1 063 232 B1 | 12/2005 |
| EP | 1 449 824 B1 | 8/2006 |
| WO | WO 2006/102243 A2 | 9/2006 |

OTHER PUBLICATIONS

Herranz et al. "An Improved One-Pot Method for Stereoselective Synthesis of the (2S,3R)-3-Amino-2-hydroxy Acids: Key Intermediates for Bestatin and Amastatin," J. Org. Chem. 1990, vol. 55, pp. 2232-2234.
Tsuda et al. "Poststatin, a New inhibitor of Prolyl Endopeptidase. III. Optical Resolution of 3-Amino-2-hydroxyvaleric Acid and absolute Configuration of Poststatin." J. Antibiotics Tokyo, 1996, vol. 49, No. 3, pp. 281-286.
Williams et al. "*dl*-Isoserine and Related Compounds," J. Org. Chem. 1985, vol. 50, pp. 91-97.

* cited by examiner

*Primary Examiner* — Taylor Victor Oh
(74) *Attorney, Agent, or Firm* — Kilpatrick Townsend & Stockton LLP

(57) ABSTRACT

The present invention relates to a process for the preparation of (2S,3S)-3-amino-N-cyclopropyl-2-hydroxyalkanamides, and their use in the preparation of HCV inhibitors and cathepsin inhibitors.

1 Claim, No Drawings

PROCESS FOR THE PREPARATION OF (3S)-3-AMINO-N-CYCLOPROPYL-2-HYDROXYALKANAMIDE DERIVATIVES

CROSS-REFERENCES TO RELATED APPLICATIONS

This application claims priority to U.S. Provisional Patent Application No. 61/035,992 filed Mar. 12, 2008, which application is incorporated herein by reference in its entirety and for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to a process for the preparation of (2S,3S)-3-amino-N-cyclopropyl-2-hydroxyalkanamide derivatives, which are intermediates useful in the synthesis of serine and cysteine protease inhibitors. In particular, the process is suitable for large scale synthesis of (2S,3S)-3-amino-N-cyclopropyl-2-hydroxypentanamide and (2S,3S)-3-amino-N-cyclopropyl-2-hydroxyhexanamide.

BACKGROUND

Hepatitis C virus (HCV) is a (+)-sense single-stranded RNA virus that is a major cause of non-A, non-B hepatitis worldwide. A large percentage of people infected with HCV develop chronic liver disease. This chronic hepatitis C infection, in turn, puts them at high risk for developing serious liver diseases such as liver cirrhosis, hepatocellular carcinoma and terminal liver disease leading to death.

Compounds having an (S)-N-cyclopropylamino-1,2-dioxoalkan-3-ylamide group, for example an (S)-N-cyclopropylamino-1,2-dioxohexan-3-ylamido group, have been shown to be useful both for the treatment of hepatitis C and related disorders, and as cathepsin S inhibitors. See, for example, U.S. Patent Application 2007/0054864 and WO2006/102243, the complete disclosures of which are hereby incorporated by reference. Accordingly, it would be desirable to have a facile synthesis of common intermediates useful in the preparation of such compounds, particularly a synthesis suitable for large scale preparation of this and similar intermediates.

SUMMARY OF THE INVENTION

In one aspect, this invention is directed to a process for the preparation of (2S,3S)-3-amino-N-cyclopropyl-2-hydroxyalkanamide derivatives, comprising:
contacting a (2S,3S)-N-cyclopropyl-3-(dibenzylamino)-2-hydroxyalkanamide derivative with hydrogen in the presence of a suitable catalyst. In one embodiment, the dibenzylaminoamide derivative is (2S,3S)-N-cyclopropyl-3-(dibenzylamino)-2-hydroxyhexanamide or (2S,3S)-N-cyclopropyl-3-(dibenzylamino)-2-hydroxypentanamide, the catalyst is a palladium catalyst, for example palladium (II) hydroxide or palladium on carbon, and the reaction is carried out in an inert solvent, typically methanol or ethanol.

In a second aspect, the invention is directed to a process for the preparation of (2S,3S)-N-cyclopropyl-3-(dibenzylamino)-2-hydroxyalkanamide derivatives, comprising
contacting a (2S,3S)-3-(dibenzylamino)-2-hydroxyalkanoic acid derivative with cyclopropylamine in an inert solvent, typically dichloromethane, in the presence of reagents suitable for amide formation. In one embodiment, the acid is (2S,3S)-3-(dibenzylamino)-2-hydroxyhexanoic acid or (2S,3S)-3-(dibenzylamino)-2-hydroxypentanoic acid, and the reagents suitable for amide formation are a mixture of 1-ethyl-3-(3'-dimethylamino-propyl)carbodiimide (EDCI) and 1-hydroxybenzotriazole (HOBT).

In a third aspect, the invention is directed to a process for the preparation of (2S,3S)-3-(dibenzylamino)-2-hydroxyalkanoic acids, comprising:
contacting a (2S,3S)-3-(dibenzylamino)-2-hydroxyalkanenitrile derivative with a strong acid. In one embodiment, the (2S,3S)-3-(dibenzylamino)-2-hydroxyalkanenitrile derivative is (2S,3S)-3-(dibenzylamino)-2-hydroxyhexanenitrile or (2S,3S)-3-(dibenzylamino)-2-hydroxypentanenitrile, and the strong acid is concentrated hydrochloric acid (12N).

The crude (2S,3S)-3-(dibenzylamino)-2-hydroxyalkanoic acid thus produced is optionally purified before proceeding with the next reaction by contacting the acid with an optically active amine in an inert solvent, recrystallizing the diastereomeric salt thus formed, and converting back to the free acid by addition of a strong acid. Typically, the optically active amine is (S)-alpha-methylbenzylamine, and the inert solvent is methyl t-butylether.

In a fourth aspect, the invention is directed to a process for the preparation of (2S,3S)-3-(dibenzylamino)-2-hydroxyhexanenitrile, comprising:
contacting an (S)-2-(dibenzylamino)alkanal derivative with sodium bisulfite in an inert solvent; and
contacting the bisulfite adduct thus formed with a cyanide salt.

In one embodiment the (S)-2-(dibenzylamino)alkanal derivative is (S)-2-(dibenzylamino)pentanal or (S)-2-(dibenzylamino)butanal, the inert solvent is aqueous methanol, and the cyanide salt is typically sodium cyanide.

In a fifth aspect, the invention is directed toward a process for the preparation of (S)-2-(dibenzylamino)alkanal derivative, comprising:
contacting an (S)-2-(dibenzylamino)-N-methoxy-N-methylalkanamide derivative with a reducing agent. In one embodiment, the (S)-2-(dibenzylamino)-N-methoxy-N-methylalkanamide derivative is (S)-2-(dibenzylamino)-N-methoxy-N-methylhexanamide or (S)-2-(dibenzylamino)-N-methoxy-N-methylpentanamide, the reducing agent is lithium aluminum hydride, and the reaction is tetrahydrofuran.

In a sixth aspect, the invention is directed toward a process for the preparation of (S)-2-(dibenzylamino)-N-methoxy-N-methylalkanamide derivatives, comprising:
a) contacting an (S)-2-aminoalkanoic acid with excess benzyl halide in the presence of a base;
b) contacting the tribenzyl compound thus formed with a base, to hydrolyze to the dibenzyl acid (S)-2-(dibenzylamino)alkanoic acid; and
c) contacting the (S)-2-(dibenzylamino)alkanoic acid with reagents suitable for amide formation, for example 1-ethyl-3-(3'-dimethylaminopropyl)-carbodiimide and 1-hydroxybenzotriazole, and contacting the complex thus formed with N,O-dimethylhydroxylamine in the presence of a tertiary base.

In step a), the acid is typically (S)-2-aminopentanoic acid or (S)-2-aminobutanoic acid, the base is typically a mixture of sodium hydroxide and potassium carbonate, or optionally potassium carbonate alone, and the reaction is carried out in an aqueous environment or ethanol. Typically, the benzyl halide is benzyl chloride or benzyl bromide.

In step b), the base is typically sodium hydroxide or lithium hydroxide, and the reaction is carried out in an aqueous environment in the presence of methanol or tetrahydrofuran.

In step c), typically the tertiary base is N-methylmorpholine, and the reaction is carried out in an inert solvent, typically methylene chloride.

In a seventh aspect, the invention relates to novel intermediates formed in the process, for example (S)-benzyl-2-(dibenzylamino)butanoate, (S)-2-(dibenzylamino)butanoic acid, (S)-2-(dibenzylamino)-N-methoxy-N-methylbutanamide, (S)-2-(dibenzylamino)butanal, (2S,3S)-3-(dibenzylamino)-2-hydroxypentanenitrile, (2S,3S)-3-(dibenzylamino)-2-hydroxypentanoic acid, (2S,3S)-N-cyclopropyl-3-(dibenzylamino)-2-hydroxypentanamide, (S)-benzyl-2-(dibenzylamino)pentanoate, (S)-2-(dibenzylamino) pentanoic acid, (S)-2-(dibenzylamino)-N-methoxy-N-methylpentanamide, (S)-2-(dibenzylamino)pentanal, (2S,3S)-3-(dibenzylamino)-2-hydroxyhexanenitrile, (2S,3S)-3-(dibenzylamino)-2-hydroxyhexanoic acid, and (2S,3S)-N-cyclopropyl-3-(dibenzylamino)-2-hydroxyhexanamide.

In an eighth aspect, the invention is directed to a process for the preparation of (2S,3S)-3-amino-N-cyclopropyl-2-hydroxyhexanamide, comprising:

a) contacting L-norvaline ((S)-2-aminopentanoic acid) with excess benzyl halide in the presence of a base;

b) contacting the tribenzyl compound thus formed ((S)-benzyl-2-(dibenzylamino)pentanoate) with a base, to hydrolyze to the acid (S)-2-(dibenzylamino)pentanoic acid;

c) contacting the (S)-2-(dibenzylamino)pentanoic acid thus formed with reagents suitable for amide formation, for example 1-ethyl-3-(3'-dimethylaminopropyl)-carbodiimide and 1-hydroxybenzotriazole, and contacting the complex thus formed with N,O-dimethylhydroxylamine in the presence of a tertiary base;

d) contacting the (S)-2-(dibenzylamino)-N-methoxy-N-methylpentanamide thus formed with a reducing agent, typically lithium aluminum hydride in tetrahydrofuran;

e) contacting the (S)-2-(dibenzylamino)pentanal thus formed with sodium bisulfite in an inert solvent; and contacting the bisulfite adduct thus formed with a cyanide salt;

f) contacting the (2S,3S)-3-(dibenzylamino)-2-hydroxyhexanenitrile thus formed with a strong acid, typically concentrated hydrochloric acid;

g) contacting the (2S,3S)-3-(dibenzylamino)-2-hydroxyhexanoic acid thus formed with cyclopropylamine in the presence of reagents suitable for amide formation, typically a mixture of 1-ethyl-3-(3'-dimethylamino-propyl) carbodiimide and 1-hydroxybenzo-triazole; and h) contacting the (2S,3S)-N-cyclopropyl-3-(dibenzylamino)-2-hydroxyhexanamide thus formed with hydrogen in the presence of a suitable catalyst, typically palladium hydroxide.

The crude (2S,3S)-3-(dibenzylamino)-2-hydroxyhexanoic acid produced in step (f) is optionally purified before proceeding with step g) by contacting the acid with an optically active amine in an inert solvent, recrystallizing the diastereomeric salt thus formed, and converting to the free acid by addition of a strong acid. Typically, the optically active amine is (S)-alpha-methylbenzylamine, and the inert solvent is methyl t-butylether.

In a ninth aspect, the invention is related to the use of (2S,3S)-3-amino-N-cyclopropyl-2-hydroxyhexanamide for the preparation of (2S,4R)-1-((S)-2-(3-tert-butylureido)-3,3-dimethylbutanoyl)-N-((S)-1-(cyclopropylamino)-1,2-dioxohexan-3-yl)-4-(7-methoxy-2-(1H-pyrazol-1-yl)quinolin-4-yloxy)pyrrolidine-2-carboxamide, comprising;

a) contacting (2S,3S)-N-cyclopropyl-3-(dibenzylamino)-2-hydroxyhexanamide with hydrogen in the presence of a suitable catalyst in an inert solvent;

b) contacting the (2S,3S)-3-amino-N-cyclopropyl-2-hydroxyhexanamide thus formed with (2S,4R)-1-(tert-butoxycarbonyl)-4-(7-methoxy-2-(1H-pyrazol-1-yl)quinolin-4-yloxy)pyrrolidine-2-carboxylic acid in the presence of reagents suitable for amide formation in an inert solvent;

c) contacting the (2S,4R)-tert-butyl 2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidine-1-carboxylate thus formed with aqueous hydrochloric acid in methanol;

d) contacting the (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidinium salt thus formed with (R)-2-(3-tert-butylureido)-3,3-dimethylbutanoic acid in the presence of reagents suitable for amide formation in an inert solvent; and e) contacting the (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide thus formed with an oxidizing agent in an inert solvent.

In one embodiment, the catalyst in step a) is palladium hydroxide and the inert solvent is methanol.

In another embodiment, in steps b) and d) the reagents suitable for amide formation are a mixture of 2-(1H-7-Azabenzotriazol-1-yl)-1,1,3,3-tetramethyluronium hexafluorophosphate (HATU) and a tertiary base, for example diisopropylethylamine, and the inert solvent is a mixture of dichloromethane and N,N-dimethylformamide.

In another embodiment, the oxidizing agent of step c) is Dess Martin periodinane reagent and the inert solvent is dichloromethane.

DETAILED DESCRIPTION OF THE INVENTION

The present invention provides processes for the preparation of a key intermediate in the synthesis of HCV inhibitors and cathepsin S inhibitors.

Previously, one method used in the synthesis of such inhibitors that include an (S)-N-cyclopropylamino-1,2-dioxoalkan-3-ylamide group has proceeded through an intermediate of formula (f), which has a t-BOC protecting group, which is then removed to provide the free amine (g). See, for example, U.S. Patent Application 2007/0054864, the complete disclosure of which is hereby incorporated by reference. The intermediates (f) and (g) were prepared as shown below.

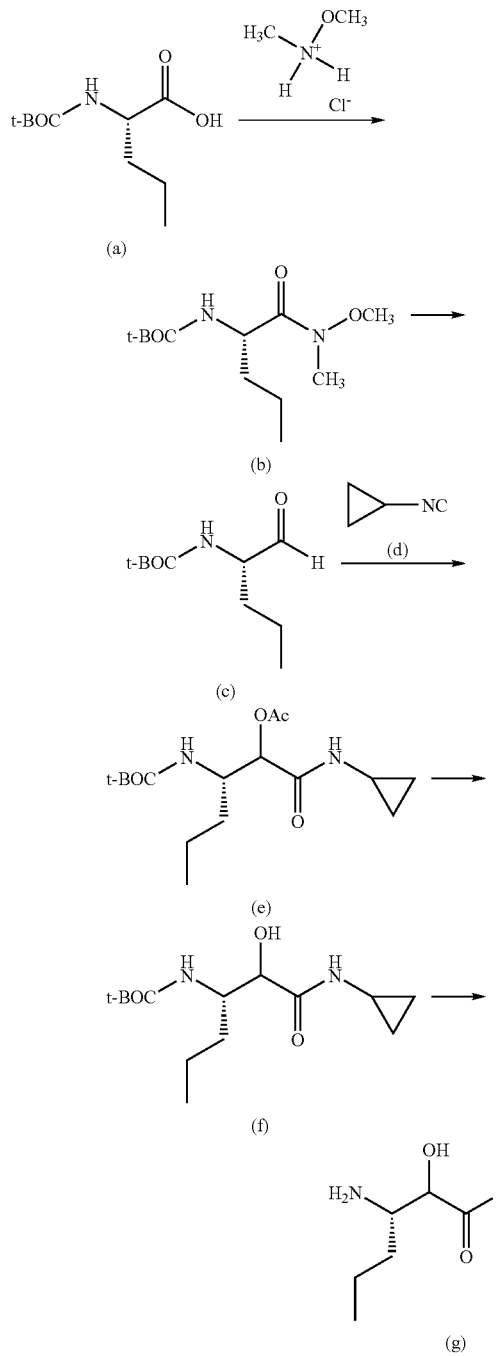

(a)
(b)
(c)
(d)
(e)
(f)
(g)

where t-BOC is t-butoxycarbonyl

The compound of formula (f) is deprotected to the free amine (g) by treatment with hydrochloric acid, which is reacted with an appropriate carboxylic acid under conditions suitable for amide formation, and the hydroxyl group of the product thus formed is oxidized to an HCV inhibitor having an (S)-N-cyclopropylamino-1,2-dioxohexanamide-3-ylamide group The above process for the preparation of (g) has several drawbacks. For example, the protected aldehyde (c) is unstable, and cannot be stored at room temperature for any length of time. Also, the reaction sequence utilizes cyclopropylisonitrile as a reactant. Cyclopropylisonitrile has a highly unpleasant and penetrating odor, and is also not stable on prolonged storage, all of which are potential disadvantages when carrying out the process, particularly on a large scale. Additionally, the compound of formula (g) is produced as a mixture of diastereomers, which potentially are difficult to crystallize in good yield on a large scale.

Accordingly, a more convenient and efficient process is desired for the preparation of inhibitors containing an (S)-N-cyclopropylamino-1,2-dioxoalkan-3-ylamide group and related compounds, particularly one that avoids the use of cyclopropylisonitrile, and is useful for large scale synthesis. Such a process is outlined in Reaction Scheme I. Bn represents a benzyl group (phenylmethylene), R is alkyl of 1-6 carbon atoms optionally substituted by cycloalkyl of 3-6 carbon atoms, for example methyl, ethyl, n-propyl, isopropyl, n-butyl, isobutyl, tert-butyl, pentyl, hexyl, cyclopropylmethyl, cyclopropylethyl, cyclobutylethyl, cyclobutylpropyl, cyclopentylethyl, cyclohexylpropyl, and the like. Inert solvent means a solvent that is inert to the conditions of the reaction being described.

"Alkyl" means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Cycloalkyl" refers to a monovalent saturated monocyclic ring containing three to eight ring carbon atoms, unless otherwise indicated e.g., cyclopropyl, cyclobutyl, cyclopentyl, cyclohexyl, and the like.

REACTION SCHEME 1

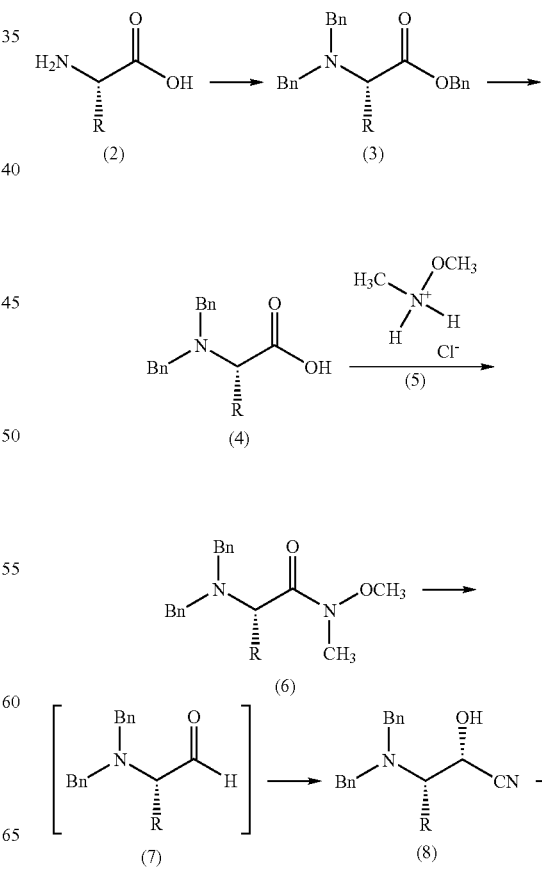

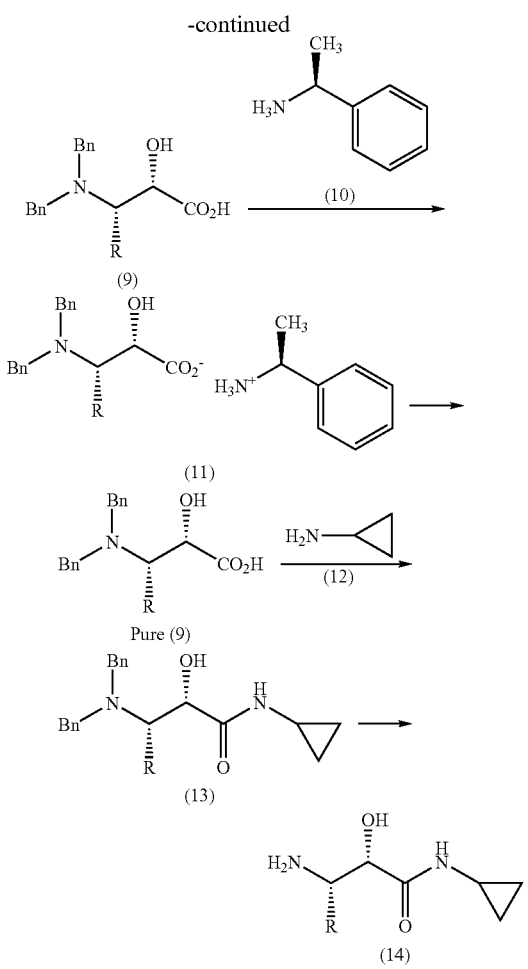

where Bn is benzyl and R is alkyl as defined above

There are several advantages of such a process. The use of benzyl groups as protecting groups provides intermediates that are stable, and, in the case of compounds (4), (8), and (9) provides compounds that are solids, which are much easier to purify on a large scale by standard techniques, for example by recrystallization. The use of benzyl groups also provides a chromophore that makes it easier to follow the progress of the reactions and their end points, and to better analyze the intermediates for chemical and stereochemical purity, whereas the t-BOC group does not. Additionally, the t-BOC group is not compatible with the reaction conditions required to convert the cyanohydrin (8) to the carboxylic acid (9). It is also noteworthy that the cyanohydrin (8) is produced as a single diastereomer, which facilitates characterization and purification on a large scale by recrystallization (because crystallization of a mixture of diastereomers can lead to lower yields due to loss of one of the isomers in the crystallization process). The same advantages are present for all subsequent intermediate steps, including the coupling of the compound of formula (14) to an appropriate carboxylic acid under conditions suitable for amide formation to produce an intermediate as a first step in the synthesis of an HCV inhibitor or cathepsin S inhibitor with an (S)-N-cyclopropylamino-1,2-dioxoalkan-3-ylamide group. Also, the intermediate of formula (13) is a stable solid, and thus serves as a purification control point, for example by slurring with a mixture of ethyl acetate and hexane; and is easily deprotected (by hydrogenation) to provide the free amine necessary for reaction with an appropriate carboxylic acid. By contrast, removal of the t-BOC group in the previous process under highly acidic conditions tends to degrade the product, for example by hydrolysis of the cyclopropyl amide, particularly when extended reaction times are required.

Step 1—Preparation of a Compound of Formula (3)

To a mixture of bases, typically sodium hydroxide and potassium carbonate, in aqueous solution, is added an (S)-2-aminoalkanoic acid, for example (S)-2-aminopentanoic acid (L-norvaline). The reaction is initially carried out at a temperature of about 0-5° C., then at about 85-95° C. To the solution thus formed is added a benzyl halide, typically benzyl bromide or benzyl chloride, and the mixture maintained at about 85-95° C. When the reaction is substantially complete, the product of formula (3) is isolated by conventional means, for example by extraction with an inert organic solvent, separation of the organic solvent layer, and removal of the solvent under reduced pressure, to provide an (S)-benzyl-2-(dibenzylamino)alkanoate derivative (3), for example (S)-benzyl-2-(dibenzylamino)pentanoate. The product can be used in the next step with no further purification.

Step 2—Preparation of a Compound of Formula (4)

The compound of formula (3) dissolved in a protic solvent, for example methanol, is contacted with an aqueous solution of a base, typically sodium hydroxide, at about 0-5° C. The reaction is conducted at about reflux temperature for about 6-24 hours. When the reaction is substantially complete, the product of formula (4) is isolated by conventional means, for example by extracting impurities with an inert solvent, acidifying the aqueous layer, extracting product with an inert solvent, removing solvent under reduced pressure, to provide an (S)-2-(dibenzylamino)alkanoic acid of formula (4).

Step 3—Preparation of a Compound of Formula (6)

The compound of formula (4) is dissolved in an inert solvent, for example dichloromethane at about 0-5° C., and reagents that promote amide formation are added, typically a mixture of 1-ethyl-3-(3'-dimethylaminopropyl)carbodiimide (EDCI) and 1-hydroxybenzotriazole (HOBT). The reaction is conducted at about room temperature for about 6-24 hours, then cooled to about 0-5° C. and then a tertiary base added, typically N-methylmorpholine, followed by N,O-dimethylhydroxylamine hydrochloride (5). The reaction mixture is maintained at about room temperature for about 12-24 hours. When the reaction is substantially complete, the product of formula (6) is isolated by conventional means, to provide an (S)-2-(dibenzylamino)-N-methoxy-N-methylalkanamide of formula (6).

Step 4—Preparation of a Compound of Formula (7)

To a solution of a reducing agent, typically lithium aluminum hydride, in an inert solvent, typically tetrahydrofuran, at about −20- to −30° C., is added the compound of formula (6), an (S)-2-(dibenzylamino)-N-methoxy-N-methylalkanamide, in an inert solvent, typically tetrahydrofuran. When the reaction is substantially complete, the product of formula (7) is isolated by conventional means, to provide an (S)-2-(dibenzylamino)alkanal of formula (7), which is used without purification in the next step.

Step 5—Preparation of a Compound of Formula (8)

The crude compound of formula (7) is dissolved in a protic solvent, for example methanol, and reacted with aqueous sodium bisulfite. The reaction is conducted at a temperature of about 0-5° C., for about 6-24 hours. To the product is added an inert solvent, for example ethyl acetate, and aqueous sodium cyanide, at a temperature of about 0-5° C. The mixture is stirred for about 2-8 hours. When the reaction is substantially complete, the product of formula (8) is isolated by conventional means, to provide a (2S,3S)-3-(dibenzylamino)-2-hydroxyalkanenitrile of formula (8). The absolute stereochemistry of this diastereomer has been shown to be the anti-isomer (2S,3S)-configuration, by conversion of the compound of formula (14) to a cyclic derivative (the oxazolidinone) with phosgene, and has been shown to be up to 99% pure as a single isomer.

Step 6—Preparation of a Compound of Formula (9)

The product of formula (8) is hydrolyzed under acidic conditions, for example by reflux in concentrated hydrochloric acid. When the reaction is substantially complete, the product of formula (9) is isolated by conventional means, for example neutralizing the acid with a base, for example aqueous sodium hydroxide solution, and extracting the product with an inert solvent immiscible with water, for example dichloromethane, to provide a crude (2S,3S)-3-(dibenzylamino)-2-hydroxyalkanoic acid of formula (9).

Step 7—Optional Purification of the Compound of Formula (9)

The crude compound of formula (9) obtained in step 6 is dissolved in a suitable inert solvent, for example methyl t-butylether, at about 0-5° C. To this cold solution is added a chiral amine, for example (S)-alpha-methylbenzylamine, and the mixture maintained at about room temperature for about 2-10 hours. The salt thus formed is separated conventionally, to provide the (S)-alpha-methylbenzylamine salt of the compound of formula (9). This salt is converted back to the free acid by conventional means, for example by treatment with a dilute acid, for example aqueous hydrochloric acid, to provide purified acid of formula (9).

Step 8—Preparation of the Compound of Formula (13)

The compound of formula (9) is dissolved in an inert solvent, for example dichloromethane at about 0-5° C., and reagents that promote amide formation added, typically a mixture of 1-ethyl-3-(3'-dimethylaminopropyl)carbodiimide (EDCI) and 1-hydroxybenzotriazole (HOBT). The reaction is allowed to warm to about room temperature for about 10 minutes, then cooled to about 0-5° C. and cyclopropylamine added. The reaction mixture is maintained at about room temperature for about 1-5 hours. When the reaction is substantially complete, the product is isolated by conventional means, to provide a (2S,3S)-N-cyclopropyl-3-(dibenzylamino)-2-hydroxyalkanamide, a compound of formula (13).

Step 8—Preparation of the Compound of Formula (14)

The compound of formula (13) is dissolved in an inert solvent, for example methanol, and a metal catalyst added, for example a palladium metal catalyst, typically palladium(II) hydroxide, at about room temperature, and the mixture stirred under hydrogen at about 40-60 psi. When the reaction is substantially complete, the product is isolated by conventional means, typically by filtering the catalyst off and removing the solvent under reduced pressure, to provide a (2S,3S)-3-amino-N-cyclopropyl-2-hydroxyalkanamide, a compound of formula (14).

One utility of the compound of formula (14) is shown in Reaction Scheme II.

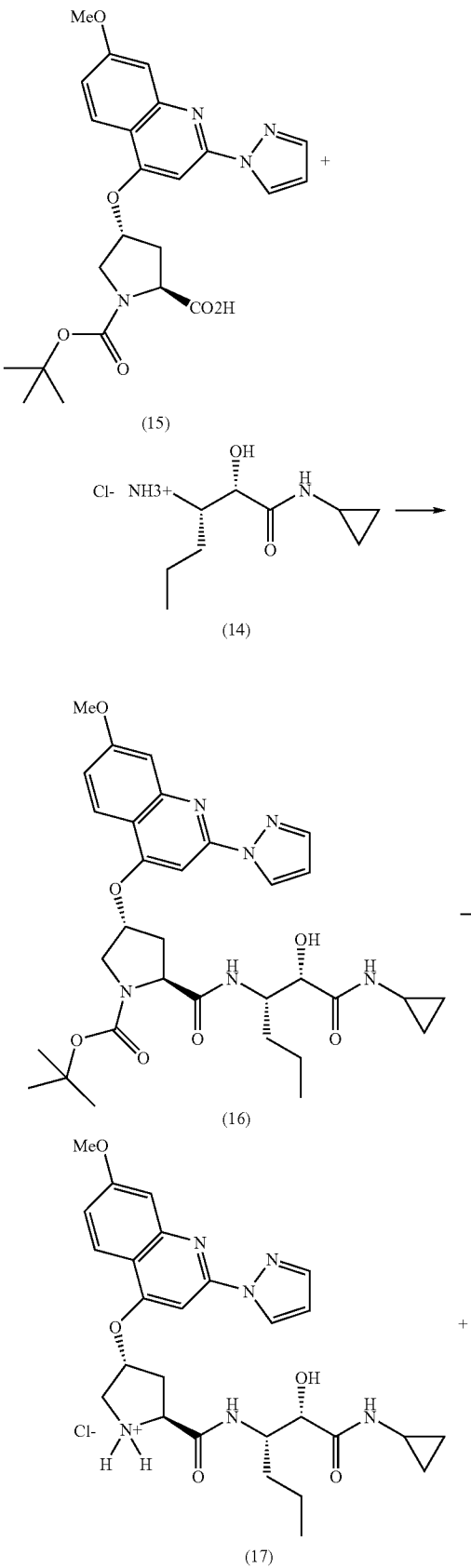

REACTION SCHEME II

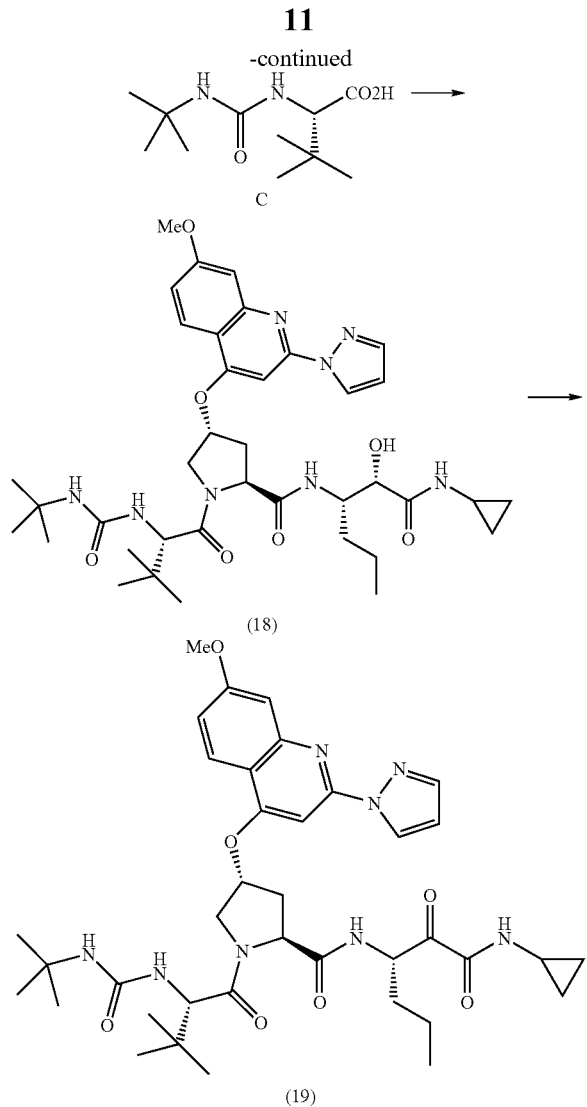

(18)

(19)

Step 1—Preparation of a Compound of Formula (16)

To a solution of the compound of formula (15) in an inert solvent, typically a mixture of dichloromethane and N,N-dimethylformamide, is added reagents that promote amide formation added, typically a mixture of 2-(1H-7-Azabenzotriazol-1-yl)-1,1,3,3-tetramethyluronium hexafluorophosphate (HATU) and a tertiary base, for example diisopropylethylamine, at about room temperature, followed by the compound of formula (14). When the reaction is substantially complete, the product is isolated by conventional means, to provide (2S,4R)-tert-butyl 2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidine-1-carboxylate, the compound of formula (16)

Step 2—Preparation of a Compound of Formula (17)

To a solution of the compound of formula (16) in an inert solvent, for example methanol, is added methanolic hydrochloric acid, typically about 10-20% dropwise. The reaction mixture is maintained at about room temperature for about 1-5 hours. When the reaction is substantially complete, the product is isolated by conventional means, to provide (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidinium chloride, the compound of formula (17).

Step 3—Preparation of a Compound of Formula (18)

To a solution of the compound of formula (17) in a polar solvent, typically dimethylsulfoxide, is added compound the compound of formula (C) and reagents that promote amide formation added, typically a mixture of 2-(1H-7-Azabenzotriazol-1-yl)-1,1,3,3-tetramethyluronium hexafluorophosphate (HATU) and a tertiary base, for example diisopropylethylamine. The reaction is conducted at about room temperature for about 1-5 hours. When the reaction is substantially complete, the product is isolated by conventional means, to provide (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide, the compound of formula (18).

Step 4—Preparation of a Compound of Formula (19)

To a solution of the compound of formula (18) in an inert solvent, for example dichloromethane, is added Dess-Martin Periodinane reagent at about room temperature for about 1 hour. Completion of the reaction was monitored by TLC analysis. When the reaction is substantially complete, the product is isolated by conventional means, to provide (2S,4R)-1-((S)-2-(3-tert-butylureido)-3,3-dimethylbutanoyl)-N-((S)-1-(cyclopropylamino)-1,2-dioxohexan-3-yl)-4-(7-methoxy-2-(1H-pyrazol-1-yl)quinolin-4-yloxy)pyrrolidine-2-carboxamide, the compound of formula (19), a compound useful as an HCV inhibitor.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (3)

A. Preparation of (S)-benzyl 2-(dibenzylamino)pentanoate

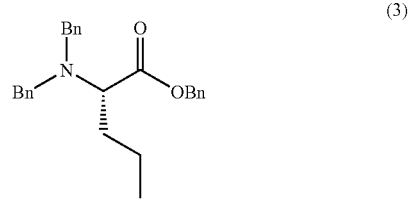 [SMILES: CCC[C@@H](C(=O)OCc1ccccc1)N(Cc1ccccc1)Cc1ccccc1]

Sodium hydroxide (0.513 Kg; 12.82 moles) and potassium carbonate (1.77 Kg, 12.82 moles) were dissolved in water (7.5 L) and cooled to 0° C. The resulting solution was treated with (S)-2-aminopentanoic acid (L-norvaline, 0.75 Kg; 6.41 moles) slowly at between 0-5° C. The stirred suspension was heated at 90° C. and benzyl bromide (4.385 Kg, 25.64 moles) was added dropwise. Heating was continued for a further 12 hours at 90° C. The reaction mixture was then cooled to ambient temperature, and extracted with ethyl acetate (2×6 liters). The layers were separated and the aqueous phase extracted twice with ethyl acetate. The combined organic extracts were dried over sodium sulfate, and the solvent removed under reduced pressure to obtain 3.3 Kg of crude (S)-benzyl 2-(dibenzylamino)pentanoate, a compound of formula (3), as a brown oil. This material was used in the next reaction without further purification.

$^{1}$H NMR (CDCl$_{3}$): δ 7.42-7.18 (15H, m, Ar—H), 5.18 (2H, q, OCH$_{2}$Ph), 3.98-3.42 (4H, q, 2 x NCH$_{2}$Ph), 3.38 (1H, t, CH), 1.8-1.2 (4H, m, CH$_{2}$), 0.79 (3H, t, CH$_{3}$).

LC-MS: 388 (M+H)$^{+}$

B. Preparation of (S)-benzyl 2-(dibenzylamino)butanoate

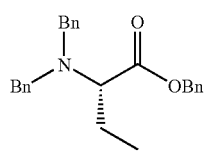 [SMILES: CC[C@@H](C(=O)OCc1ccccc1)N(Cc1ccccc1)Cc1ccccc1]

Similarly, following the procedure of Example 1A, but replacing (S)-2-aminopentanoic acid with (S)-2-aminobutanoic acid, (S)-benzyl 2-(dibenzylamino)butanoate is prepared.

C. Preparation of other (S)-benzyl 2-(dibenzylamino)alkanoate Derivatives of Formula (3)

Similarly, following the procedure of Example 1A, but replacing (S)-2-aminopentanoic acid with amino acids of formula (2):

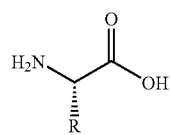

(2)

where R is alkyl as defined above, other (S)-benzyl 2-(dibenzylamino)alkanoate derivatives of formula (3) are prepared.

EXAMPLE 2

Preparation of a Compound of Formula (4)

A. Preparation of (S)-2-(Dibenzylamino)pentanoic acid

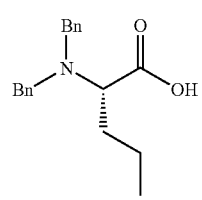

(4)

The crude (S)-benzyl 2-(dibenzylamino)pentanoate (3) (2.2 Kg) was dissolved in methanol (5.5 L). A previously prepared, cold (0-5° C.) solution of sodium hydroxide (568 g; 14.2 mol) in water (6 L) was added to the solution of (3), and the resulting mixture heated at 90° C. for 20 hours. The reaction mixture was then allowed to cool to ambient temperature, and the methanol evaporated under reduced pressure. The residue was diluted with water (25 L), and extracted with methyl t-butyl ether/hexane (1:1; 2×5 L) to remove the benzyl alcohol formed in the hydrolysis. The basic aqueous layer was acidified to pH 2 with 6M aqueous hydrochloric acid (4 L), then extracted with ethyl acetate (2×8 L). The combined organic extracts were dried over sodium sulfate and the solvent removed under reduced pressure, to afford a semi solid, which was washed with hexanes (8 L) to provide 1.12 Kg of (S)-2-(dibenzylamino)pentanoic acid, a compound of formula (4), as a white solid.

$^{1}$H-NMR (CDCl$_{3}$): δ 7.42-7.2 (10H, m, Ph-H), 3.75 (4H, s, NCH$_{2}$Ph), 3.38 (1H, t, CH), 1.8 (2H, m, CH$_{2}$), 1.45 (2H, m, CH$_{2}$), 0.79 (3H, t, CH$_{3}$).

LC-MS: 298 (M+H)$^{+}$

B. Preparation of (S)-benzyl 2-(dibenzylamino)butanoic acid

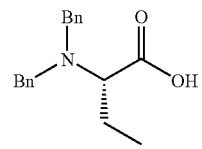

Similarly, following the procedure of Example 2A, but replacing (S)-benzyl 2-(dibenzylamino)pentanoate with (S)-benzyl 2-(dibenzylamino)butanoate, (S)-2-(dibenzylamino) butanoic acid is prepared.

C. Preparation of other (S)-benzyl 2-(dibenzylamino)alkanoic acids of Formula (4)

Similarly, following the procedure of Example 2A, but replacing (S)-benzyl 2-(dibenzylamino)pentanoate with other compounds of formula (3):

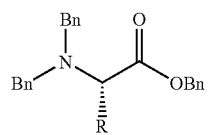

(3)

where R is alkyl as defined above, other (S)-benzyl 2-(dibenzylamino)alkanoic acids of formula (4) are prepared.

EXAMPLE 3

Preparation of a Compound of Formula (6)

A. Preparation of (S)-2-(Dibenzylamino)-N-methoxy-N-methylpentanamide

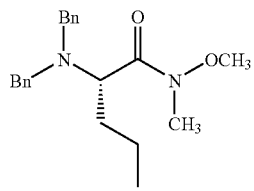 [SMILES: CCC[C@@H](C(=O)N(C)OC)N(Cc1ccccc1)Cc1ccccc1]

(S)-2-(dibenzylamino)pentanoic acid (1.57 Kg; 5.286 mol) was dissolved in dry dichloromethane (9.42 L) under a nitrogen atmosphere and cooled to 0-5° C. The resulting solution was treated with N-hydroxybenzotriazole (HOBt; 928 g; 6.875 mol) followed by 1-ethyl-3-(3'-dimethylaminopropyl)carbodiimide (EDCI, 1.51 Kg; 7.931 mol;) at 0-5° C. The reaction mixture was stirred for 3 hours at ambient temperature, then treated with N-methylmorpholine (NMM; 1.62 Kg; 16.07 mol) followed by N,O-dimethylhydroxylamine hydrochloride (1.29 Kg; 13.22 mol) at 0° C. The reaction mixture was stirred at ambient temperature for 15 hours, then water (2.5 L) added, and the mixture stirred for 10 minutes. The organic layer was separated, washed with 1% aqueous hydrochloric acid, followed by saturated aqueous sodium bicarbonate, then brine solution. The organic phase was dried over sodium sulfate, filtered and concentrated under reduced pressure to provide (S)-2-(dibenzylamino)-N-methoxy-N-methylpentanamide, a compound of formula (6), as a syrupy oil.

$^1$H-NMR (CDCl$_3$): δ 7.42-7.15 (10H, m, Ph-H), 3.6-3.4 (5H, m, NCH$_2$Ph+CH), 3.23-3.0 (6H, 2s, NMe+OMe), 1.4-1.8 (4H, m, CH$_2$), 0.85 (3H, t, CH$_3$).

LC-MS: 340 (M+H)$^+$

B. Preparation of (S)-2-(dibenzylamino)-N-methoxy-N-methylbutanamide

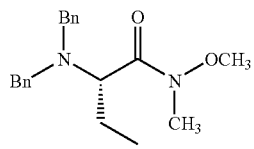

Similarly, following the procedure of Example 3A, but replacing (S)-2-(dibenzylamino)pentanoic acid with (S)-2-(dibenzylamino)butanoic acid, (S)-2-(dibenzylamino)-N-methoxy-N-methylbutanamide is prepared.

C. Preparation of other (S)-2-(dibenzylamino)-N-methoxy-N-methylalkanamides of Formula (6)

Similarly, following the procedure of Example 3A, but replacing (S)-2-(dibenzylamino)pentanoic acid with other compounds of formula (4):

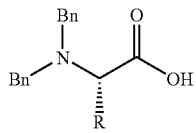

where R is alkyl as defined above, other (S)-2-(dibenzylamino)-N-methoxy-N-methyalkanamides of formula (6) are prepared.

EXAMPLE 4

Preparation of a Compound of Formula (7)

A. Preparation of (S)-2-(Dibenzylamino)pentanal

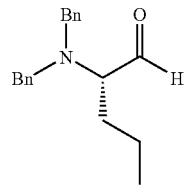

To anhydrous tetrahydrofuran (1.5 L) previously cooled to −20° C. to −30° C. was added solid lithium aluminum hydride (33.5 g; 0.882 mol; 120 mole %) slowly with stirring. A solution of (S)-2-(dibenzylamino)-N-methoxy-N-methylpentanamide (6) (250 g; 0.735 mol) in anhydrous tetrahydrofuran (1 L) at −30° C. was slowly added to the above mixture under a nitrogen atmosphere. The reaction was continued for 2 hours at −30° C., monitoring progress of the reaction by TLC analysis (ethyl acetate/hexane, 1:9). Upon completion of the reaction, the excess reagent was quenched by the dropwise addition of ethyl acetate (1 L) and ice-cold water (300 ml) at −30° C. The insoluble salts were filtered through celite, the filtrate diluted with water (3 L), and the product extracted into ethyl acetate (2 L). The combined ethyl acetate layers were washed with water (2 L), dried over sodium sulfate, filtered, and solvent removed under reduced pressure to provide (S)-2-(dibenzylamino)pentanal (7) (195 g) as a light yellow oil, which was used without purification in the next step.

$^1$H-NMR (CDCl$_3$): δ 9.75 (1H, s, CHO), 7.40-7.20 (10H, m, Ph-H), 3.75 (4H, q, NCH$_2$Ph), 3.15 (1H, t, CH), 1.80-1.20 (4H, m, CH$_2$), 0.85 (3H, t, CH$_3$)

B. Preparation of (S)-2-(dibenzylamino)butanal

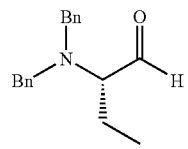

Similarly, following the procedure of Example 4A, but replacing (S)-2-(dibenzylamino)-N-methoxy-N-methylpentanamide with (S)-2-(dibenzylamino)-N-methoxy-N-methylbutanamide, (S)-2-(dibenzylamino)butanal is prepared.

C. Preparation of other (S)-2-(dibenzylamino)alkanals of Formula (7)

Similarly, following the procedure of Example 4A, but replacing (S)-2-(dibenzylamino)-N-methoxy-N-methylpentanamide with other compounds of formula (6):

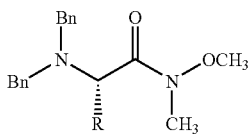
(6)

where R is alkyl as defined above, other (S)-2-(dibenzylamino)alkanals of formula (7) are prepared.

EXAMPLE 5

Preparation of a Compound of Formula (8)

A. Preparation of (2S,3S)-3-(Dibenzylamino)-2-hydroxyhexanenitrile

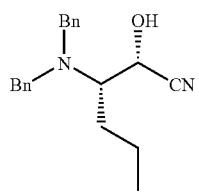 [SMILES: CCC[C@@H]([C@H](O)C#N)N(Cc1ccccc1)Cc1ccccc1]

To a solution of (S)-2-(dibenzylamino)pentanal (125 g; 0.444 mol) in methanol (375 mL) at 0-5° C. was added a previously cooled (0-5° C.) aqueous solution of sodium bisulfite (69.39 g, 0.667 mol; 150 mole %) in water (530 mL). The reaction mixture was stirred at 0-5° C. for 14 hours. A solution of sodium cyanide (32.02 g; 0.667 mol; 150 mol %) in water (402 mL), followed by ethyl acetate (1.25 L) was added to the above reaction mixture at 0° C. Stirring was continued at ambient temperature for 5 hours, monitoring progress of the reaction by TLC analysis (ethyl acetate/hexane, 1:9). Once the reaction was complete, the ethyl acetate layer was separated, washed with water (2×750 mL) and dried over sodium sulfate. The organic extract was concentrated under reduced pressure, washed with hexanes (200 mL), to provide 94 g of crude product as an off-white solid.

It should be noted that analysis of the cyanohydrin of formula (8) by chiral HPLC at 210 nm showed it to be >99% of a single diastereomer. The absolute configuration of this diastereomer was shown to be (2S,3S) as described below.

$^1$H-NMR (CDCl$_3$): δ 7.4-7.2 (10H, m, Ph-H), 4.68 (1H, bd, OH), 4.30 (1H, m, CHOH), 4.15, 3.44 (4H, 2xd, NCH$_2$Ph), 2.98 (1H, m, CH), 1.98-1.20 (4H, m, CH$_2$), 1.0 (3H, t, CH$_3$).

LC-MS: 308 (M+H)$^+$

B. Preparation of (2S,3S)-3-(Dibenzylamino)-2-hydroxypentanenitrile

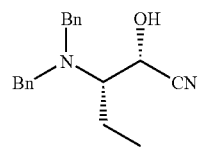

Similarly, following the procedure of Example 5A, but replacing (S)-2-(dibenzylamino)pentanal with (S)-2-(dibenzylamino)butanal, (2S,3S)-3-(dibenzylamino)-2-hydroxypentanenitrile is prepared.

C. Preparation of other (2S,3S)-3-(Dibenzylamino)-2-hydroxyalkanenitrile of Formula (8)

Similarly, following the procedure of Example 5A, but replacing (S)-2-(dibenzylamino)pentanal with other compounds of formula (7):

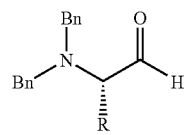
(7)

where R is alkyl as defined above, other (2S,3S)-3-(dibenzylamino)-2-hydroxyalkanenitrile of formula (8) are prepared.

EXAMPLE 6

Preparation of a Compound of Formula (9)

A. Preparation of (2S,3S)-3-(Dibenzylamino)-2-hydroxyhexanoic acid

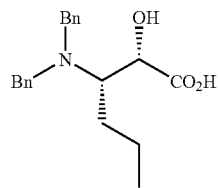 [SMILES: CCC[C@@H]([C@H](O)C(=O)O)N(Cc1ccccc1)Cc1ccccc1]

To (2S,3S)-3-(dibenzylamino)-2-hydroxyhexanenitrile (93.0 g; 0.301 mol) was added 12N hydrochloric acid (465 mL). The resulting mixture was heated to reflux (100° C.) for 3 hours, monitoring progress of the reaction by TLC analysis (ethyl acetate/hexane, 1:1). After TLC analysis indicated that the reaction was complete, the reaction mixture was cooled, and the pH was adjusted to 6-7 using 6N aqueous sodium hydroxide solution (930 mL). The product was extracted with two portions of dichloromethane (2×700 mL), and the combined organic phases were dried over sodium sulfate. After filtration the solvent was removed under reduced pressure, to give 95.0 g (96%) of (2S,3S)-3-(dibenzylamino)-2-hydroxyhexanoic acid as a solid.

¹H-NMR (CDCl₃): δ 7.4-7.2 (10H, m, Ph-H), 4.30-4.18 (4H, m, OH, CH and NCH₂Ph), 3.75 (2H, m, NCH₂Ph), 3.19 (1H, m, CH), 2.09-1.38 (4H, m, CH₂), 0.98 (3H, t, CH₃).
LC-MS: 328 (M+H)⁺

B. Preparation of (2S,3S)-3-(Dibenzylamino)-2-hydroxypentanoic acid

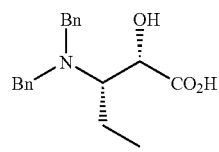

Similarly, following the procedure of Example 6A, but replacing (2S,3S)-3-(dibenzylamino)-2-hydroxyhexanenitrile with (2S,3S)-3-(dibenzylamino)-2-hydroxypentanenitrile, (2S,3S)-3-(dibenzylamino)-2-hydroxypentanoic acid is prepared.

C. Preparation of other (2S,3S)-3-(Dibenzylamino)-2-hydroxyalkanoic acids of Formula (9)

Similarly, following the procedure of Example 6A, but replacing (2S,3S)-3-(dibenzylamino)-2-hydroxyhexanenitrile with other compounds of formula (8):

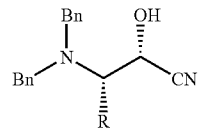

(8)

where R is alkyl as defined above, other (2S,3S)-3-(dibenzylamino)-2-hydroxyalkanoic acids of formula (9) are prepared.

EXAMPLE 7

Purification of (2S,3S)-3-(dibenzylamino)-2-hydroxyhexanoic acid by Salt Formation with (S)-α-Methylbenzylamine

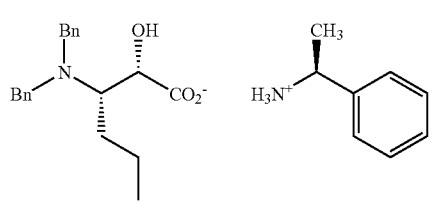

(11)

The crude (2S,3S)-3-(dibenzylamino)-2-hydroxyhexanoic acid (25.0 g; 76.4 mmol) was dissolved in methyl t-butylether (125 mL) and cooled to 0-5° C. (S)-α-methylbenzylamine (10; 9.26 g; 76.4 mmol) was added slowly, then the reaction mixture maintained at ambient temperature for 4 hours, during which time solid formation was observed. The mixture was treated with hexane, and the solid filtered off. The filter cake was washed with hexane and dried under vacuum, to provide 25.0 g (72.9%) of the salt (11) as a white solid.

The salt (25.0 g) was dissolved in dichloromethane (100 mL) and washed with a 1% aqueous hydrochloric acid solution (100 mL). The dichloromethane phase was dried over sodium sulfate, and solvent removed under reduced pressure, to provide 15.0 g of the purified acid (2S,3S)-3-(dibenzylamino)-2-hydroxyhexanoic acid (9) as a white solid.

¹H-NMR (CDCl₃): δ 7.4-7.2 (10H, m, Ph-H), 4.18-3.98 (4H, m, OH, NCH₂Ph), 3.75 (2H, m, NCH₂Ph), 3.02 (1H, m, CH), 1.82-1.35 (4H, m, CH₂), 0.9 (3H, t, CH₃)

B. Similarly, Other Compounds of Formula (9) can be Purified if Desired.

EXAMPLE 8

Preparation of a Compound of Formula (13)

A. Preparation of (2S,3S)-N-cyclopropyl-3-(dibenzylamino)-2-hydroxyhexanamide

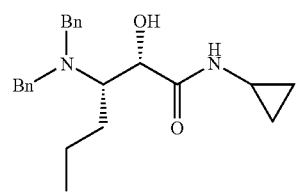 [SMILES: CCC[C@@H]([C@H](O)C(=O)NC1CC1)N(Cc1ccccc1)Cc1ccccc1]

To a previously cooled solution of pure (2S,3S)-3-(dibenzylamino)-2-hydroxyhexanoic acid (52.0 g; 0.159 mol) in dichloromethane (520 mL) at 0-5° C. was added at 0° C. 1-hydroxybenzotriazole (HOBT, 32.2 g; 0.238 mol) followed by 1-ethyl-3-(3'-dimethylaminopropyl)carbodiimide (EDCI, 45.5 g; 0.238 mol). The mixture was stirred for 10 minutes at ambient temperature. The progress of the reaction was monitored by TLC (methanol/methylene chloride, 5:95). After 10 minutes, cyclopropylamine (18.13 g; 0.318 mol) was added at 0° C., and the mixture was stirred at ambient temperature for 3 hours. Reaction progress was again monitored by TLC. Upon completion of the reaction, water was added (500 ml), the organic layer separated, and washed with brine (500 mL). The organic layer was separated, dried over sodium sulfate, and solvent removed under reduced pressure to provide crude (2S,3S)-N-cyclopropyl-3-(dibenzylamino)-2-hydroxyhexanamide as a semi-solid. This semi-solid was suspended in hexanes (250 mL) and filtered. The process was repeated, to provide 35 g of pure (2S,3S)-N-cyclopropyl-3-(dibenzylamino)-2-hydroxyhexanamide as a white solid.

¹H-NMR (CDCl₃): δ 7.4-7.2 (10H, m, Ph-H), 4.01 (1H, d, OH), 3.78-3.45 (4H, 2xd, NCH₂Ph), 2.96 (1H, m, CH), 2.49 (1H, m, CH—(CH₂)₂) 2.0-1.22 (4H, m, CH₂), 0.95 (3H, t, CH₃), 0.67 (2H, CH₂ of cyclopropane), 0.31 (2H, CH₂ of cyclopropane)

B. Preparation of (2S,3S)-N-cyclopropyl-3-(dibenzylamino)-2-hydroxypentanamide

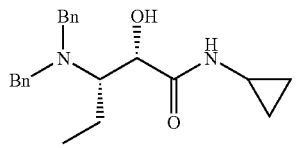 [SMILES: CC[C@@H]([C@H](O)C(=O)NC1CC1)N(Cc1ccccc1)Cc1ccccc1]

Similarly, following the procedure of Example 8A, but replacing (2S,3S)-3-(dibenzylamino)-2-hydroxyhexanoic acid with (3S)-3-(dibenzylamino)-2-hydroxypentanoic acid, (2S,3S)-N-cyclopropyl-3-(dibenzylamino)-2-hydroxypentanamide is prepared.

C. Preparation of other (2S,3S)-N-cyclopropyl-3-(dibenzylamino)-2-hydroxy-alkanamides of Formula (13)

Similarly, following the procedure of Example 8A, but replacing (2S,3S)-3-(dibenzylamino)-2-hydroxyhexanoic acid with other compounds of formula (9):

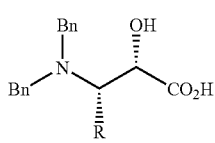

(9)

where R is alkyl as defined above, other (2S,3S)-N-cyclopropyl-3-(dibenzylamino)-2-hydroxyalkanamides of formula (13) are prepared.

EXAMPLE 9

Preparation of a Compound of Formula (14)

A. Preparation of (2S,3S)-3-amino-N-cyclopropyl-2-hydroxyhexanamide

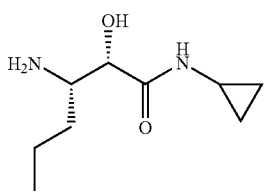

To a solution of (2S,3S)-N-cyclopropyl-3-(dibenzylamino)-2-hydroxyhexanamide (35.0 g) in methanol (350 mL) was carefully added palladium hydroxide on carbon (20% Pd(OH)$_2$/C, 7.0 g), and the mixture was stirred under hydrogen at 50 psi for 2 hours. The mixture was filtered through Celite, and washed with methanol (150 mL). The solvent was evaporated under reduced pressure, to provide a light yellow solid, which was further washed with hexanes (2×75 mL), to give (2S,3S)-3-amino-N-cyclopropyl-2-hydroxyhexanamide (16.4 g).

$^1$H-NMR (CDCl$_3$): δ 7.58 (1H, bd, CONH), 3.81 (1H, bd, OH), 3.12 (1H, m, CH), 2.78 (1H, m, CH), 2.21 (2H, bd, NH$_2$), 1.20-1.58 (4H, m, CH$_2$), 0.92 (3H, t, CH$_3$), 0.81 (2H, m, CH$_2$ of cyclopropane), 0.51 (2H, CH$_2$ of cyclopropane).

B. Preparation of (2S,3S)-3-amino-N-cyclopropyl-2-hydroxypentanamide

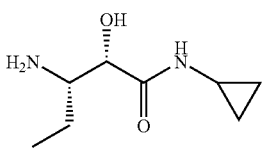

Similarly, following the procedure of Example 9A, but replacing (2S,3S)-N-cyclopropyl-3-(dibenzylamino)-2-hydroxyhexanamide with (2S,3S)-N-cyclopropyl-3-(dibenzylamino)-2-hydroxypentanamide, (2S,3S)-3-amino-N-cyclopropyl-2-hydroxypentanamide is prepared.

C. Preparation of other (2S,3S)-3-amino-N-cyclopropyl-2-hydroxyalkanamides of Formula (14)

Similarly, following the procedure of Example 9A, but replacing (2S,3S)-N-cyclopropyl-3-(dibenzylamino)-2-hydroxyhexanamide with other compounds of formula (13):

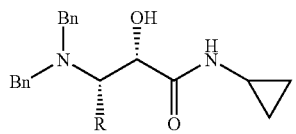

(13)

where R is alkyl as defined above, other (2S,3S)-3-amino-N-cyclopropyl-2-hydroxyalkanamides of formula (14) are prepared.

Determination of the Absolute Stereochemistry of (2S,3S)-3-amino-N-cyclopropyl-2-hydroxyalkanamide (2S,3S)-3-Amino-N-cyclopropyl-2-hydroxyhexanamide was converted to the corresponding oxazolidinone by reaction with triphosgene. The resulting product was analyzed by proton NMR and the stereochemistry of the product was determined by the coupling constants (J value) for the protons at C-4 and C-5 of the cyclized derivatives. Based on literature values for similar products (Tsuda, M.; Muraoka, Y.; Nagai, M.; Aoyagi, T.; Takeuchi, T. J. Antibiotics 1996, 49, 281-286, Herranz, R.; Castro-Pichel, J.; Vinuesa, S.; Garcia-López. M. T. J. Org. Chem. 1990, 55, 2232, Williams, T. M.; Crumbie, R.; Mosher, H. S. J. Org. Chem. 1985, 50, 91-97), the cis-isomer (J$_{4,5}$=8.8 Hz) was obtained exclusively from the reaction of (2S,3S)-3-amino-N-cyclopropyl-2-hydroxyhexanamide with triphosgene, indicating that the absolute configuration of the-3-amino-N-cyclopropyl-2-hydroxyhexanamide derivative was (2S,3S).

EXAMPLE 10

Preparation of a Compound of Formula (16)

A. Preparation of (2S,4R)-tert-butyl 2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidine-1-carboxylate

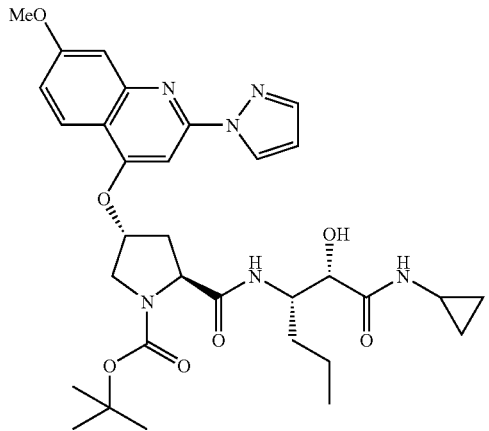 [SMILES: CCC[C@H](NC(=O)[C@@H]1C[C@@H](Oc2cc(-n3cccn3)nc3cc(OC)ccc23)CN1C(=O)OC(C)(C)C)[C@H](O)C(=O)NC1CC1]

To a solution of (2S,4R)-1-(tert-butoxycarbonyl)-4-(7-methoxy-2-(1H-pyrazol-1-yl)quinolin-4-yloxy)pyrrolidine-2-carboxylic acid (5.0 g, 11.0 mmol) dissolved in a mixture of methylene chloride (135 mL) and N,N-dimethylformamide (45 mL) was added 2-(1H-7-Azabenzotriazol-1-yl)-1,1,3,3-tetramethyluronium hexafluorophosphate (HATU, (4.97 g, 42.6 mmol) and diisopropylethylamine (7.2 mL, 41.11 mmol), followed by the hydrochloride salt of (2S,3S)-3-amino-N-cyclopropyl-2-hydroxyhexanamide (2.45 g, 11.0 mmol). The reaction mixture was stirred at room temperature for 2 hours under nitrogen atmosphere. Completion of reaction was monitored by TLC. The reaction mixture was diluted with methylene chloride (200 mL) and washed with 10% hydrochloric acid (100 mL), followed by with 10% sodium bicarbonate solution (100 mL), water (100 mL) and brine (100 mL). The organic layer was dried over sodium sulfate, filtered, and the filtrate concentrated under reduced pressure to provide 5.4 g (67.6%) of (2S,4R)-tert-butyl 2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy) pyrrolidine-1-carboxylate as an off-white solid (HPLC purity: 98.59% by area, HPLC retention time: 14.74 minutes).

$^1$H NMR (DMSO-d6, 500 MHz): δ 8.78 (s, 1H), 7.92 (d, 1H), 7.84 (s, 1H), 7.64 (m, 2H), 7.41 (m, 1H), 7.28 (s, 1H), 7.17 (d, 1H), 6.61 (s, 1H), 5.62-5.40 (m, 2H), 4.4 (bs, 1H), 4.05 (bs, 1H), 3.9 (s, 3H), 3.88-3.7 (m, 3H), 2.7 (m, 2H), 2.3 (bs 1H), 1.39 (s, 9H), 1.18 (m, 4H), 0.8 (m, 3H), 0.6-0.4 (m, 4H).

EXAMPLE 11

Preparation of a Compound of Formula (17)

Preparation of (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy) pyrrolidinium Chloride

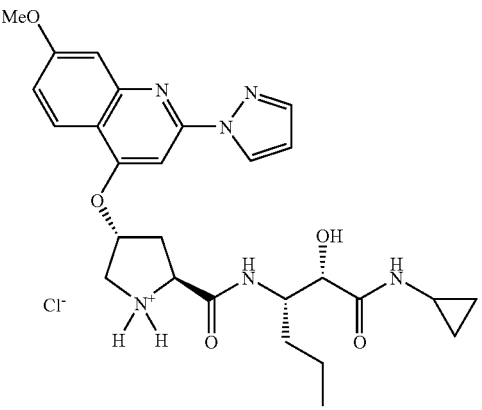 [SMILES: CCC[C@H](NC(=O)[C@@H]1C[C@@H](Oc2cc(-n3cccn3)nc3cc(OC)ccc23)C[NH2+]1)[C@H](O)C(=O)NC1CC1 ; [Cl-]]

To a cooled solution (0-5° C.) of (2S,4R)-tert-butyl 2-((2S, 3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidine-1-carboxylate (3.0 g; 4.82 mmol) in methanol (10 mL) was added 17% methanolic hydrochloric acid (20 mL) dropwise. The reaction mixture was stirred at room temperature for 2 hours under nitrogen atmosphere. Completion of the reaction was monitored by TLC. Methyl t-butylether (50 mL) was added to the mixture and stirred for 10 minutes. The obtained solid was filtered and dried to yield 2.45 g (98%) of (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidinium chloride (HPLC purity: 97.74% by area; HPLC retention time: 13.30 minutes), which was used without further purification in the next step.

EXAMPLE 12

Preparation of a Compound of Formula (18)

Preparation of (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide

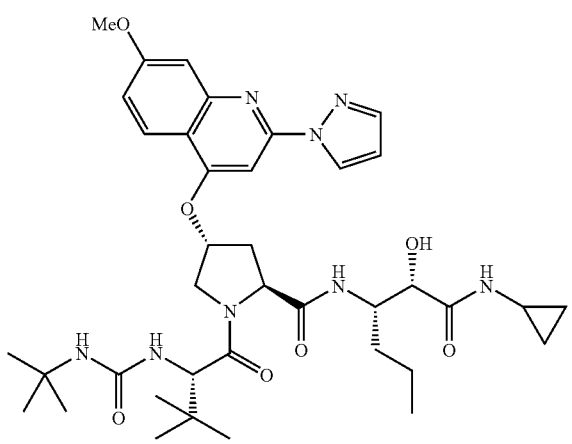 [SMILES: CCC[C@H](NC(=O)[C@@H]1C[C@@H](Oc2cc(-n3cccn3)nc3cc(OC)ccc23)CN1C(=O)[C@@H](NC(=O)NC(C)(C)C)C(C)(C)C)[C@H](O)C(=O)NC1CC1]

To a solution of (2S,4R)-2-((2S,3S)-1-(cyclopropylamino)-2-hydroxy-1-oxohexan-3-ylcarbamoyl)-4-(7-methoxy-2-(1H-pyrazol-1-yl)quinolin-4-yloxy)pyrrolidinium chloride (6.3 g, 11.2 mmol) in dimethylsulfoxide (20 mL) was added (R)-2-(3-tert-butylureido)-3,3-dimethylbutanoic acid (2.33 g, 10.2 mmol), 2-(1H-7-Azabenzotriazol-1-yl)-1,1,3,3-tetramethyluronium hexafluorophosphate (HATU, 4.74 g, 12.1 mmol) followed by diisopropylethylamine (4.95 g, 38.4 mmol), and the reaction mixture was stirred at room temperature for 3 hours under nitrogen atmosphere. Completion of the reaction was monitored by TLC analysis. The reaction mixture was diluted with water and the resulting solid was filtered and dried under reduced pressure to yield 6.3 g (71.6%) of (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide (HPLC purity: 99.2% by area; HPLC retention time: 15.06 minutes).

EXAMPLE 13

Preparation of a Compound of Formula (19)

Preparation of (2S,4R)-1-((S)-2-(3-tert-butylureido)-3,3-dimethylbutanoyl)-N-((S)-1-(cyclopropylamino)-1,2-dioxohexan-3-yl)-4-(7-methoxy-2-(1H-pyrazol-1-yl)quinolin-4-yloxy)pyrrolidine-2-carboxamide

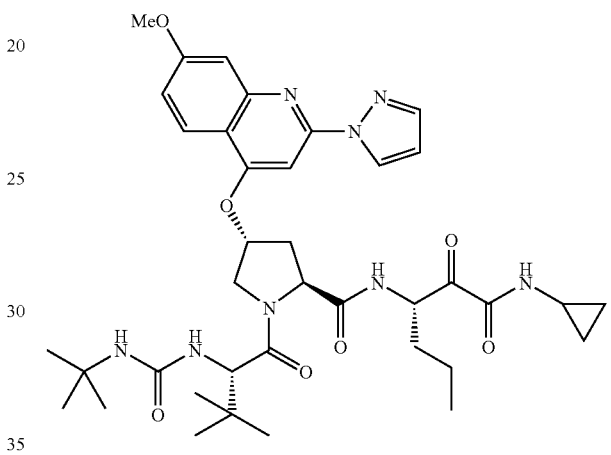

To a solution of (2S,4R)-1-((S)-2-(3-tert-butylureido)-3,3-dimethylbutanoyl)-N-((2S,3S)-1-(cyclopropylamino)-2-hydroxy-1-oxohexan-3-yl)-4-(7-methoxy-2-(1H-pyrazol-1-yl)quinolin-4-yloxy)pyrrolidine-2-carboxamide (2.0 g, 2.72 mmol) in methylene chloride (10 mL) was added the Dess-Martin Periodinane reagent (2.29 g, 5.44 mmol), and the reaction mixture was stirred at room temperature for 1 hour. Completion of the reaction was monitored by TLC analysis. Upon completion the reaction mixture was diluted with water (100 mL) and the organic layer was separated. The aqueous layer was washed with methylene chloride (2×30 mL), and the combined organic layers were washed with saturated sodium bisulfite (20 mL) followed by sodium bicarbonate solution (20 mL), and dried over sodium sulfate. The solution was filtered, the filtrate concentrated under reduced pressure, and the resulting residue was stirred with hexane (10 mL). The solid was filtered and dried to provide 1.75 g (87.8%) of (2S,4R)-1-((S)-2-(3-tert-butylureido)-3,3-dimethylbutanoyl)-N-((S)-1-(cyclopropylamino)-1,2-dioxohexan-3-yl)-4-(7-methoxy-2-(1H-pyrazol-1-yl)quinolin-4-yloxy)pyrrolidine-2-carboxamide as white solid (HPLC purity: 97.3% by area; HPLC retention time: 22.58 minutes).

$^1$H NMR (DMSO-d6, 500 MHz): δ 8.8 (s, 1H), 8.7 (s, 1H), 8.21 (d, 1H), 8.18 (d, 1H), 7.84 (s, 2H), 7.43 (s, 1H), 7.28 (s, 1H), 6.99 (d, 1H), 6.61 (s, 1H), 5.96 (m, 1H) 5.48 (s, 1H), 5.0 (bs, 1H), 4.58 (m, 2H), 4.22 (d, 1H), 3.88 (s, 3H), 3.84 (m, 1H), 2.78(m, 1H), 2.58 (m, 1H), 2.18 (m, 1H), 1.78 (bs, 1H), 1.4 (m, 3H), 1.21 (s, 9H), 0.91 (s, 9H), 0.84 (m, 4H), 0.68-0.58 (m, 4H).

LC-MS: 733.0 (M+H)$^+$

What is claimed is:
1. A compound chosen from the group consisting of (S)-2-(dibenzylamino)-N-methoxy-N-methylpentanamide, (2S,3S)-3-(dibenzylamino)-2-hydroxyhexanenitrile, (2S,3S)-3-(dibenzylamino)-2-hydroxyhexanoic acid, and (2S,3S)-3-(dibenzylamino)-2-hydroxyhexanoic acid.

* * * * *